United States Patent [19]

Zakim

[11] Patent Number: 5,733,507
[45] Date of Patent: Mar. 31, 1998

[54] BIOLOGICAL CELL SAMPLE HOLDER FOR USE IN INFRARED AND/OR RAMAN SPECTROSCOPY ANALYSIS HOLDER

[75] Inventor: David S. Zakim, Armonk, N.Y.

[73] Assignee: InPhoCyte, Inc., White Plains, N.Y.

[21] Appl. No.: 485,366

[22] Filed: Jun. 7, 1995

[51] Int. Cl.⁶ ................................................. B01L 11/00
[52] U.S. Cl. ..................... 422/101; 422/58; 422/102; 422/104
[58] Field of Search ................ 422/58, 101, 82.05, 422/82.09, 104, 102; 356/36, 244

[56] References Cited

U.S. PATENT DOCUMENTS

| | | | |
|---|---|---|---|
| 1,311,017 | 7/1919 | Skoglund | 422/101 X |
| 3,379,083 | 4/1968 | Ard . | |
| 3,515,490 | 6/1970 | Dreyfus et al. | 356/244 |
| 3,521,963 | 7/1970 | Bader | 356/244 |
| 4,729,949 | 3/1988 | Weinreb et al. | 435/30 |
| 4,787,988 | 11/1988 | Bertoncini et al. | 422/101 X |
| 4,849,061 | 7/1989 | Relyea | 422/101 X |
| 5,038,039 | 8/1991 | Wong et al. | 250/339 |
| 5,139,685 | 8/1992 | de Castro et al. | 422/101 X |
| 5,168,162 | 12/1992 | Wong et al. | 250/339 |
| 5,171,995 | 12/1992 | Gast et al. | 250/339 |
| 5,174,162 | 12/1992 | Miyake et al. | 73/864.21 |
| 5,240,861 | 8/1993 | Bieri | 436/178 |
| 5,266,209 | 11/1993 | Knight et al. | 210/691 |
| 5,270,212 | 12/1993 | Horiuchi et al. | 436/45 |
| 5,308,483 | 5/1994 | Sklar et al. | 210/232 |
| 5,408,306 | 4/1995 | Anderson | 356/36 |
| 5,470,757 | 11/1995 | Gagnon et al. | 422/58 X |
| 5,484,572 | 1/1996 | Katakura et al. | 422/101 |

FOREIGN PATENT DOCUMENTS

| | | |
|---|---|---|
| 932551 | 8/1973 | Canada . |
| 991438 | 6/1976 | Canada . |
| 1036385 | 8/1978 | Canada . |
| 1138218 | 12/1982 | Canada . |
| 1222566 | 6/1987 | Canada . |
| 1242593 | 10/1988 | Canada . |
| 1261256 | 9/1989 | Canada . |
| 1269929 | 6/1990 | Canada . |
| 2019865 | 6/1990 | Canada . |
| 2012291 | 11/1990 | Canada . |
| 2005622 | 6/1991 | Canada . |
| 2007267 | 7/1991 | Canada . |
| 2036031 | 1/1992 | Canada . |
| 2103446 | 12/1992 | Canada . |
| 2106507 | 3/1994 | Canada . |
| 1057078 | 6/1994 | Canada . |
| 2136423 | 9/1994 | Canada . |
| 9015981 | 12/1990 | WIPO . |
| 9300580 | 1/1993 | WIPO . |

OTHER PUBLICATIONS

P.Jeannesson et al, *Anal. Biochem.* 1983, 129, 305–309.
Aldrich Chemical Catalog 1988, pp. 1947–1949.
Fisher Scientific Catalog, 1988, pp. 418–421.
Blout, E.R. and Mellors, R.C.; "Infrared Spectra Of Tissues"; (1949); Science 110, 137.
Wood, D.L. "Infrared Microspectrum Of Living Muscle Cell"; (1951); Science 114, 36.

(List continued on next page.)

*Primary Examiner*—Arlen Soderquist
*Attorney, Agent, or Firm*—Hale and Dorr LLP

[57] ABSTRACT

A biological cell sample holder for use in infrared and/or Raman spectroscopy. The sample holder includes a rectangular body that has a stepped opening through the center. The body is transparent to infrared and Raman energy. A window is disposed in the stepped opening. The window has pores of a predetermined size to allow fluid to pass through the window but retain cells of interest on the window. There also is an assembly that is used to cause the collection and concentration of cells on the window. The assembly includes a flask with a first outlet that connects to a vacuum source and a second outlet that connects to a drain system. The flask has a open top end. A frit sealingly engages the top end of the flask. The frit is hollow and has a nipple extending from the top surface of the frit. The fruit has a top surface that is adapted to fit the sample holder.

4 Claims, 6 Drawing Sheets

OTHER PUBLICATIONS

Schwarz, H.P., Riggs H.E., Cameron, W., Beyer, E., Jaffe, B., and Trombetta, L.: "Infrared Spectroscopy Of Tissue. Effect Of Insulin Shock" (1951); Proc. Soc. Exptl. Biol. Med. 76, 267.

Wood, D.L. and Sutherland, G.B.B.M.; "Infrared Spectra Of Muscle Cells"; (1952); Fed. Proc. 11, 175.

Morales, M.F. and Cecchini, L.P. "Some Studies On The Infrared Absorption Of The Contractile System Of Skeletal Muscle"; (1951); J. Cell Comp. Physiol. 37, 107.

Schwarz, H.P., Riggs, H.E. Glick, C., McGrath, J., Cameron, W., Beyer, B., Bew, E., Jr., and Childs, R,; "Infrared Spectroscopy Of Brain Tissue. A Lipid Fraction In Normal And Irradiated Adult and Fetal Rats"; (1952); Proc. Soc. Exptl. Biol. Med. 80, 467.

Schwarz, H.P., Riggs, H.E. Glick, C., McGrath, J., Childs, R., Bew, E., Jr. and Stone, F. "Infrared Spectroscopy Of Liver Glycogen In Normal And Irradiated Adult And Fetal Rats"; (1954); Proc. Soc. Exptle Biol. Med. 85, 96.

Manfait, M. and Theophanides, T.; "Fourier Transform Infrared Spectra Of Cells Treated With The Drug Adriamycin"; (1983); Biochem. Biophys. Res. Communs. 116, 321.

Benedetti, E., Papineschi, F., Vergamini, P., Consolini, R., and Spremolla, G.; "New Possibilities Of Research In Chronic Lymphatic Leukemia Cells (CLL)–I"; (1984); Leukemia Research 8, 483.

Bendetti, E., Palatresi, M.P., Vergamini, P., Papineschi, F., and Spremolla, G.; "New Possibilities Of Research In Chronic Lymphatic Leukemia By Means Of Fourier Transform–Infrared Spectroscopy–II"; (1985); Leukemia Research, 9, 1001.

Wong, P.T.T., Zahab, D.M., Narang, S.A., and Sung, W.L.; "High Pressure Infrared Spectroscopic Study Of Human Proinsulin Gene Expression In Live *Escherichia Coli* Cells"; (1987); Biochem. Biophys. Res. Communs., 146, 232.

Auger, M., Jarrell, H.C., Smith I.C.P. Wong, P.T.T., Siminovitch, D.J., and Mantsch, H.M.; "Pressure–Induced Exclusion of a Local Anesthetic from Model and Nerve Membranes"; (1987); Biochemistry 26, 8513.

Spremolla, G., Benedetti, E., Vergamini, P., Andreucci, M.C., Macchia, P.; "An Investigation of Acute Lymphoblastic Leukemia (ALL) in Children by Means of Infrared Spectroscopy. Part IV"; (1988); Haematologica 73, 21–24.

Takahashi, H., French, S.W., and Wong, P.T.T.; "High Pressure Fourier Transform Infrared Spectroscopic Study on Molecular Structure of Lipids and Proteins in the Liver of Rats Chronically Fed Ethanol"; (1989); Hepatology 10, 705.

Rigas, B, Morgello, S., Goldman, I.S., and Wong, P.T.T.; "Human colorectal cancers display abnormal Fourier–transform infrared spectra"; (1990); Proc. Nat'l Acad. Sci. U.S.A. 87, 8140–8144.

Wong, P.T.T. and Rigas, B.; "Infrared Spectra of Microtome Sections of Human Colon Tissues"; (1990); Appl. Spectros. 44, 1715.

Bendetti, E., Teodori, L., Trinca, M.L., Vergamini, P1, Salvati, F., Mauro, F., and Spremolla, G.; "A New Approach to the Study of Human Solic Tumor Cells by Means of FT–IR Microspectroscopy"; (1990); Appl. Spectros. 44, 1276–1280.

Choo, L–P., Jackson, M.,, Halliday, W.C., and Mantsch, H.M.; "Infrared spectroscopic characterisation of multiple sclerosis plaques in the human central nervous system"; (1993); Biochim. Biophys. Acta 1182, 335–337.

Schmidt–Ullrich, R., Verma, S.P., and Wallach, D.F.H.; "Concanavalin a Stimulation Modifies the Lipid and Protein Structure of Rabbit Thymocyte Plasma Membranes. A Laser Raman Study"; (1976); Biochim. Biophys. Acta 426, 477–488.

Verma, S.P., and Wallach, D.F.H.; "Erythrocyte membranes undergo cooperative, pH–sensitive state transitions in the physiological temperature range: Evidence from Raman spectroscopy"; (1976); Proc. Nat'l Acad. Sci., USA 73, 3558–3561.

Frank, C.J., McCreery, R.L., Redd, D.C.B., and Gansler, T.S.; "Detection of Silicone in Lymph Nod Biopsy Speciments by Near–Infrared Raman Spectroscopy"; (1993); Appl. Spectros. 47, 387–390.

East, E.J., Chang, R.C.C., Yu, N–T, and Kuck, J.F.R.; "Raman Spectroscopic Measurement of Total Sulfhydryl in Intact Lens As Affected by Aging and Ultraviolet Irradiation"; (1978); J. Biol. Chem. 253, 1436–1441.

Wong, P.T.T., Goldstein, S.M., Grekin, R.C., Godwin, T.A., Pivik, C., and Rigas, B.; "Distinct Infrared Spectroscopic Patterns of Human Basal Cell Carcinoma of the Skin"; (1993); Cancer Res. 53, 762–765.

Wong, P.T.T., Wong, R.K., Caputo, T.A., Godwin, T.A., and Rigas, B.; "Infrared spectroscopy of exfoliated human cervical cells: Evidence of extensive structural changes during carcinogenesis"; (1991); Proc. Natl. Acad. Sci. USA 88, 10988–10992.

Yu, N–T, DeNagel, D.C., Ho, D.J–Y, and kuck J.F.R.; "Ocular Lenses in (Spiro, T.G., ed.)"; (1987); Biological Applications of Raman Spectroscopy, vol. 1, John Wiley & Sons, N.Y., N.Y., pp. 47–81.

Sokolov, K.V., Byramova, N.E., Mochalova, L.V., Tuzikov, A.B., Shiyan, S.D., Bovin, N.V., and Nabiev, I.R.; "Dectection of Sialic Acid Residues and Studies of Their Organization in Normal and Tumor $a_1$–"Acid Glycoproteins as Probed by Surface Enhanced Raman Spectroscopy"; (1993); Appl. Spectros. 47, 535–538.

Baraga, J.J., Feld, M.S., and Rava, R.P.; "Rapid Near–Infrared Raman Spectroscopy of Human Tissue with a Spectrograph and CCD Detector"; (1992); Appl. Spectros. 46, 187–190.

Abraham, J.L. and Etz, E.S.; "Molecular Microanalysis of Pathological Specimens in situ with a Laser–Raman Microprobe"; (1979); Science 206, 716–717.

Parker, F.S. and Ans, R.; "Infrared Studies of Human and Other Tissues by the Attenuated Total Reflection Technique"; (1967); Anal. Biochem. 18, 414–422.

Riddle, J.W., Kabler, P.W., Kenner, B.A., Bordner, R.H., Rockwood, S.W., and Stevenson, H.J.R.; "Bacterial Identification by Infrared Spectrometry"; (1956) J.Bacteriol. 72, 593–603.

Ozaki, Y., Mizuno, A., and Kaneuchi, F.; "Structural Differences between Type I and Type IV Collagen in Biological Tissues Studied in Vivo by Attenuated Total Reflection/Fourier Transform Infrared Spectroscopy"; (1992); Appl. Spectros. 46, 626–630.

Helm, D., Labischinski, H., Schallen, G., and Naumann, D.; "Classification and identification of bacteria by Fourier–transform infrared spectroscopy"; (1991); J. Gen Microbiol. 137, 69–79.

Ghiamati, E., Manoharan, R., Nelson, W.H., and Sperry, J.F.; "UV Resonance Raman Spectra of Bacillus Spores"; (1992); Appl. Spectros. 46, 357–364.41.

Polavarapu, P., Chen, G—C. and Deng, Z.; "Polarization–Division Interferometry: Approach for Biomedical Infrared Imaging"; (1994); Soc. Appl. Spect. vol. 48, 1403–1409.

Polavarapu, P. and Chen, G–C.; "Polarization–Division Interferometry: Far–Infrared Dichroism"; (1994); Appl. Spect. vol. 48, 1410–1418.

BIOLOGICAL CELL SAMPLE HOLDER FOR USE IN INFRARED AND/OR RAMAN SPECTROSCOPY ANALYSIS HOLDER

FIELD OF THE INVENTION

The present invention relates to sample holders that are used for holding biological cells that are to be analyzed by infrared and/or Raman spectroscopy.

BACKGROUND OF THE INVENTION

Examination of cells and tissues, referred to here as diagnostic pathology, remains a critical step for reaching a medical diagnosis and selecting the most appropriate therapy for patients. The practice of pathology is limited in reaching definitive diagnoses in many instances because of the difficulty in identifying morphological changes in individual cells that correlate with clinical hallmarks of disease. This is an especially significant problem when cells and not intact blocks of tissue are available for examination.

The accuracy and clinical value of microscopic examinations of cells, which may form a basis for making definitive pathological and clinical diagnoses, is becoming increasingly important and may provide a method of especially detecting stages of precancer and cancer without the need for tissue. This method also is attractive because cells are easier, safer, and cheaper to obtain than tissue, which is available usually via surgical procedures.

The easy accessibility to cells as compared to tissue makes it possible to use such cells for screening healthy populations for evidence of early stages of diseases, such as cancer. Cervical cells, for example, are examined to detect precancer and/or early stages of cancer of the cervix; cells in urine are examined for evidence of early stages of urogenital cancer; cells in sputum are examined for early diagnosis of lung cancer. These kinds of "cytological" tests are becoming increasingly important in the practice of medicine and for public health. This is true despite the evidence that the clinical value of cytological examinations is limited and often suspect because of the high incidence of false-negative results. Cytologic testing also is beset with a high incidence of false-positive results. Both of these results impact negatively on patient confidence and add unnecessarily to the costs of health care.

The incidence of cancer is rising as the incidence of other diseases decrease and people live longer. As such, cancer will continue to be a major health problem for years to come. The best approach to managing the burden of the cancer problem is to find the disease in its precancerous stages and then to prevent the emergence of frank cancer from precancerous cells. The way to this end is better methods for detecting cells in a precancerous stage of disease and for showing the extent to which precancerous disease approaches frank cancer.

An alternative to the traditional method of subjective, microscopic examination of stained cells for detecting precancerous disease and early stages of cancers is to assess the chemical and physical properties of the molecules within cells. The logic of this approach is that normality or abnormality in the chemical and physical properties of the molecules in cells is the basis for health and disease. Changes in the chemical and physical properties of molecules in cells precede and underlie the changes in morphology that pathologists search for microscopically as evidence of disease.

It is known that the vibrational spectra of whole cells, e.g., infrared spectroscopy and Raman spectroscopy, are sensitive methods for measuring whether the molecules in cells are normal or abnormal. It also is known that abnormalities in the vibrational spectra of cells correlate with pathological diagnoses made by microscopic examination of the tissues and cells. Copending application Ser. No. 08/523,972 titled A System and Method for Diagnosis of Disease by Infrared Analysis of Human Tissues and Cells, and filed Jun. 7, 1995, demonstrates that infrared spectroscopy of cells detects disease that cannot be detected by microscopic examination of cells, detects the evolution of normal cells through the continuum of the precancerous changes that eventuate in cancer, detects the evolution of cells through stages of dysplasia that proceeds by different detailed pathways in the accumulation of genotypic and phenotypic abnormalities, and detects the presence of viral infection of cells.

The use of spectroscopy for studying cells, i.e., describing in detail how light of different frequencies interacts with the molecules in cells, is in its infancy as a medical technology. There is, however, a need for a rapid, inexpensive method for the preparation of cells for examination by vibrational spectroscopy. Conventional methods of preparing cells for pathological examination, e.g., fixing, embedding, and staining of cells, prior to microscopic examination are not particularly useful for preparing cells for spectroscopic examination. Moreover, the methods used by spectroscopists to study inanimate matter were not useful for preparing cells for vibrational spectroscopy examination for medical diagnosis. This is because such methods are time consuming, labor intensive, and expensive. Also, what is being used by spectroscopists for study of cells requires a high degree of diligence and expertise on the part of the operator, which further inhibits the general application of the methods of vibrational spectroscopy for the diagnosis of disease.

Principally, there are three known ways to prepare cells for examination by vibrational spectroscopy. The first is no preparation at all. This method requires that cells in their natural state be added to a suitable sample holder and analyzed in the presence of small amounts of water. Second, cells may be placed on a sample holder and any water removed by drying. Third, cells may be isolated, dried, and incorporated into KBr discs. Moreover, the method of the direct addition of cells to infrared windows (of $BaF_2$) by cytocentrifugation also has been used.

All of these methods have significant problems such as expense, time, and limited availability of qualified people to do it. However, cells, as they are collected from tissues, from patients, from the body fluids of patients, from cells in culture, or otherwise, cannot be used directly in sample preparation method just described.

In order to put the problems in perspective, the specification will consider, for example, the problem of examining cervical cells by infrared spectroscopy. Cells are collected from the cervix by scraping with a brush or spatula. For conventional cytology, the cells are smeared directly from the brush or spatula onto glass slides. This method can not be used as preparation method for vibrational spectroscopy because the beam of light in the spectrometer cannot cover the area of the typical smear. Moreover, there is difficulty in controlling the thickness of cells and mucous deposited on the slide. There also may be some difficulty in fixing cells with materials that can be washed off completely so as not to interfere with spectral analysis of the cells. Lastly, materials that are used for slide material, which are transparent to mid-infrared frequencies of light, are relatively expensive.

Rather than smearing, cells can be removed from the collecting brushes and spatulas by vigorously shaking them in a fluid medium. Next, the cells in the fluid medium are concentrated and then examined. This concentration is independent of the exact set of conditions under which spectra will be obtained. If the concentrated cells are examined directly without drying, the amount of water relative to cells must be quite small or the water will detrimentally effect the result because of water's avid absorption of infrared light.

As described, cells may be prepared by drying and then examining the dried cells. Examination of dried cells also cannot be used for vibratory spectroscopy without finally concentrating the cells. Concentration is necessary because only small volumes of cellular suspensions (in the microliter range) can be added at one time to suitable sample holders for vibrational spectroscopy. Adding an appropriate number of cells to suitable infrared sample holders, for example, depends on adding, serially, several microliter acquits of cells in suspension, allowing each aliquot of the sample to dry on the sample holder before adding the next aliquot. This is a very time consuming process that is not appropriate for clinical use, i.e., it takes as long as 20 to 30 minutes, for small volumes of sample (about 20 µl) to dry.

Even with the dried cells, there will be artifacts unless the cells are fixed. Fixation of cells in this context adds considerable complexity, labor, cost, and the requirements of skill and diligence. Fixatives that are contemplated also must be removed from the cells by extensive washing prior to collecting spectra from the cells. This step or set of steps cannot be accomplished within the confines of currently available sample holders usable for vibratory spectroscopy.

A sample preparation method that accomplishes concentration and drying involves the incorporation of cells into KBr disks. This method depends on the prior concentration of cells followed by drying. Using this method, one gains no advantage over the direct addition of concentrated cells to sample holders.

Concentrating cells may be accomplished by centrifugation, which isolates the cells from the suspending fluid. The concentration of cells is not difficult to achieve by centrifugation, but it requires specialized equipment, time, and labor. Also, the need to concentrate cells by centrifugation makes it difficult to automate the process of adding cells to the appropriate sample holders. For example, in the case of cervical cells suspended in some type of aqueous medium or cells suspended in body fluids, the suspension of cells is centrifuged and the supernatant removed by aspiration or decantation. In the case of cervical cells, the cells are suspended in a relatively small volume of fluid, which is easy to remove by centrifugation in small centrifuges. When the cells are from body fluids, however, the volume of fluid can be considerable, e.g., a liter or more, which complicates the process of concentration by centrifugation.

Once cells are concentrated as a pellet in the bottom of a centrifuge tube, a small aliquot of concentrated cells is pipetted directly onto a variety of suitable sample holders. The cells can be examined in the wet state or the cells can be dried on the sample holder prior to examination. Examination of cells in the wet state requires a second window for the sample holder in order to confine the wet sample to a closed system, which increases costs and labor in cleaning the sample holder.

A complication of examining cells in the dry state, already stated, is that drying a sample of 20 to 40 µl on a sample holder at room temperature requires 20 to 30 minutes. During this time unfixed cell, autodigest their components, which introduces artifacts into the spectra collected from such cells.

Figure 1:
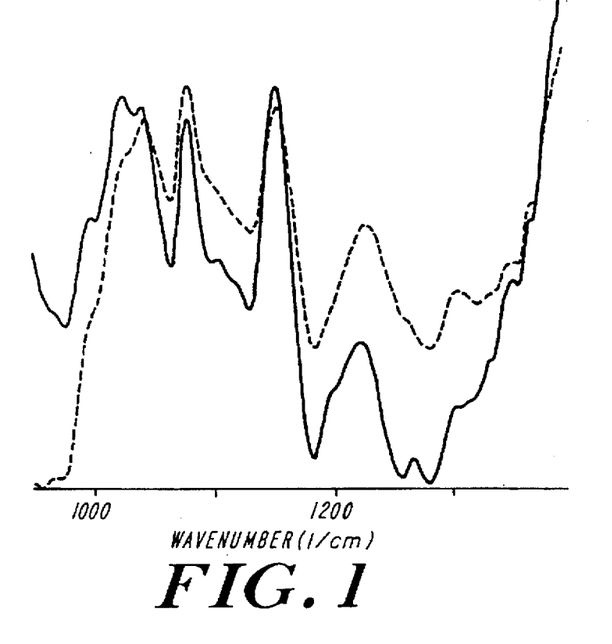
FIG. 1 shows a first comparison of spectral waveforms for unfixed cells.

The problem caused by allowing unfixed cells to stand at room temperature, even for relatively brief times, is illustrated by the spectra shown in FIG. 1. The spectrum in the solid line is an infrared spectrum of cervical cells collected 10 minutes prior to the collection of the spectrum in the dashed line on the same sample of unfixed cells on the same sample holder. Note how the spectrum in the region of 1023 $cm^{-1}$ was altered by the metabolic activity of the unfixed cells.

Figure 2:
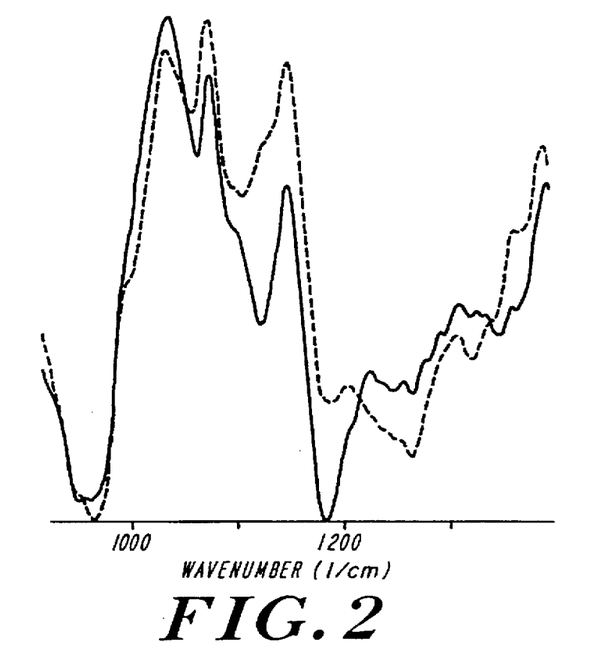
FIG. 2 shows a second comparison of spectral waveforms for unfixed cells.

FIG. 2 compares two spectra of unfixed cervical cells obtained within a few hours of each other. Here again, there are significant changes in the spectra of the unfixed cells over time.

Figure 3:
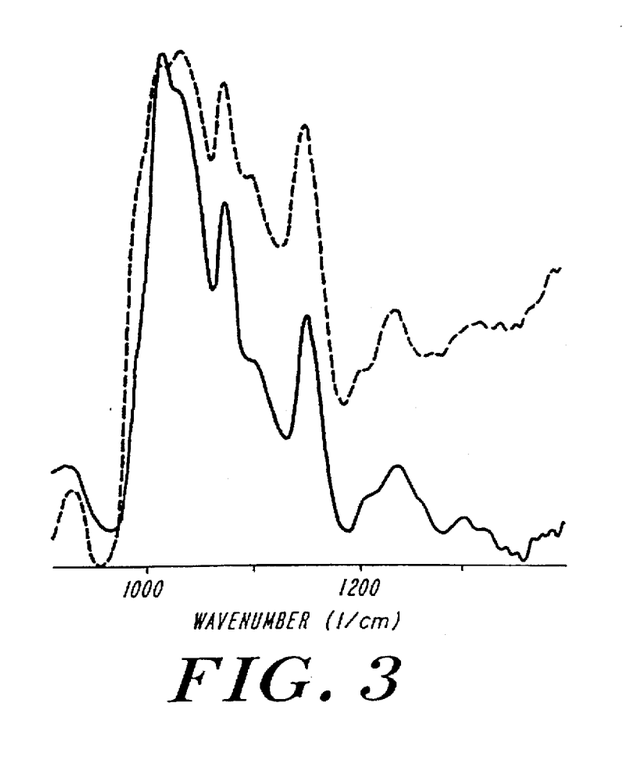
FIG. 3 shows a comparison of spectral waveforms for fixed and unfixed cells.

FIG. 3 compares spectra of cervical cells that were unfixed (dashed line) and fixed (solid line). The time differential between the unfixed and fixed samples was 30 minutes, which was the duration of time required to add cells to the window of a convention infrared sample holder and to dry them at 20° C. FIG. 3 shows how fixation of cells prevents short term, metabolically-induced changes in the spectral features of unfixed cervical cells. These examples make plain that the spectral examination of cells is best carried out on fixed cells because fixing prevents the metabolic function of cells. Otherwise, there is no certain way to control for the effects of cell viability on spectral features after cells are added to the sample holder. These examples also demonstrate that in the absence of prior fixation, heated-drying is not advantageous because heating speeds up the rate of autodigestion of unfixed cells.

The foregoing provides evidence that conventionally, the examination of human cells, or cells derived from any other source, via infrared spectroscopy is based on preparing samples individually, one at a time, in a time consuming way. These prior methods not only require that multiple steps to transfer cells from suspensions to a suitable sample holder but also end up introducing artifacts into the analytical spectra unless the cells are fixed. These methods are expensive, time-consuming, labor intensive, not amenable to automation, require centrifuges, and depend on the skill and diligence of the operator. Such methods also do not lend to the rapid preparation of large numbers of samples at low cost with minimal skill and diligence by the operator.

Conventional methods for detection of cervical cancer accounts for between 60,000,000 and 80,000,000 examinations of cervical cells each year in the U.S. The limitations referred to above prevent the full exercise of the capacity of the technology of vibrational spectroscopy which could replace conventional examinations. In particular, the limitations of the sample holder, loading of the sample holder with cells, and fixation of these cells remain paramount issues to be solved.

A separate but related difficulty in examining cervical cells, either by standard cytology or vibrational spectroscopy, is that the cervix is not a completely homogeneous organ. For example, it is recognized and recommended that samples of cells be obtained and examined separately from the endo- and the exocervix. This recommendation is almost never followed because of the economics of carrying out the test. These two samples of cells per patient require two separate examinations and double the real cost of performing the test. Therefore, the method of detecting early stages of cancer of the cervix or precancerous disease of the cervix is compromised by taking only one sample that may contain a mixture of endo- and exocervical cells.

The method of vibrational spectroscopy is not only inherently superior to cytology as a method for detecting disease in cells, it also is inherently cheaper to examine cervical cells, or other types of cells, than standard cytological methods. But the difficulty of preparing samples via conventional methods also will compromise the total amount of information that can be collected from cells using infrared spectroscopy. The economics of preparing samples for spectroscopic examination, in the absence of better methods for preparing these samples, will dictate the collection of only one sample of cervical cells per patient per examination or that specimens from the endo- and exocervical regions will be combined prior to preparing samples and examining their combined vibrational spectra. As such, the method of preparing samples for spectroscopic examination will have a significant impact on the collection of spectral data and on the amount of clinically useful information that can be derived from proper sampling of the cells of patients.

There is a need, therefore, for better methods for processing cells from the point of their collection from patients to their actual analysis by vibrational spectroscopy.

SUMMARY OF THE INVENTION

The present invention is a biological cell sample holder for use in infrared and/or Raman spectroscopy. The present invention allows the addition of a suspension of cells and other components in fluid medium to the window of an infrared sample holder that is porous and selectively retains cells. According to the sample holder of the present invention, cells are trapped on the surface of the window while all other components are filtered through the window. This obviates the need to concentrate cells by some method independent of placing them on the window. At the same time, trapping the cells on a porous window makes it possible to wash the cells extensively, treat them chemically in many different ways, and then to wash away any contaminants that might alter the vibrational spectra. This includes the ability to remove any contaminants that might be added to the collecting medium to facilitate preparation of the cells.

The present invention requires no change in the manner in which doctors collect cells from patients. For example, with respect to the cervix, doctors can collect cells by the method of the current Pap test, by fine needle aspiration of solid tissues, or with respect to other areas, in conventional ways from the sputum, urine, cerebrospinal fluid, ascitic fluid, pleural fluid, or any other body fluid. Moreover, the present invention also is directly applicable to the collection of cells in any form that may exist or can be made to exist in a fluid medium.

The present invention provides a novel method for adding collected cells to suitable sample holders that hold the cells in an analytical beam of light for the purpose of obtaining a vibrational spectrum of the cells. The vibrational spectrum can be in any range of the infrared region and can be obtained by infrared, Raman or resonance Raman spectroscopy. The present invention also can be applied to collecting spectra by transmission or reflectance spectroscopy.

The present invention includes sample holder with a window region. Once the cells to be analyzed are placed on the window region, an analytical light beam is shown through cells and the window region. The beam of analytical light must pass without interference through the window material. The window region is transparent to light of the frequencies of interest for the analysis to be performed and does not react with components in the sample holder.

In the present invention, the window region, in addition to the optical requirements just described, serves the purpose of providing a means for concentrating the material of interest as it is placed on the window and then a means for treating the sample on the window in a wide range of different ways, all of which enhance the amount of spectral information that can be collected from the cells.

DESCRIPTION OF THE INVENTION

The present invention is a biological cell sample holder for use in infrared and/or Raman spectroscopic analysis. The present invention principally will be described in the context of processing cervical cells for analysis by vibrational spectroscopy. However, it is understood that the present invention applies to any type of cell or source of cells. For example, cells from any body fluid, including blood can be processed in the same manner as cervical cells. Further, cells in experimental systems, e.g., cells in culture, whether human cells, animal cells, plant cells, normal cells, and diseased cells, can be processed by the present invention.

Figure 4A:
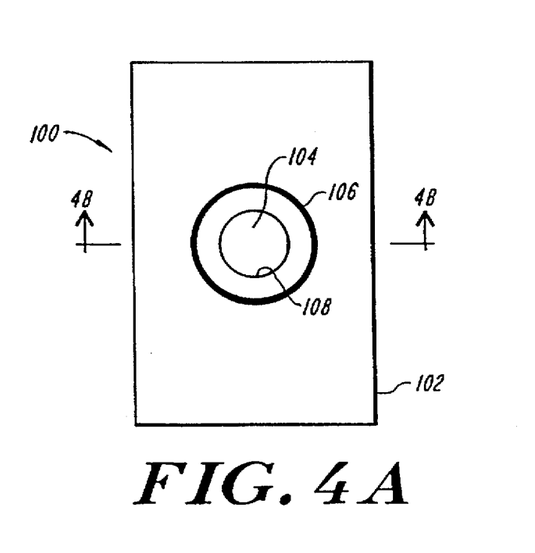
FIG. 4A shows a top view of the sample holder of the present invention.
Figure 4B:
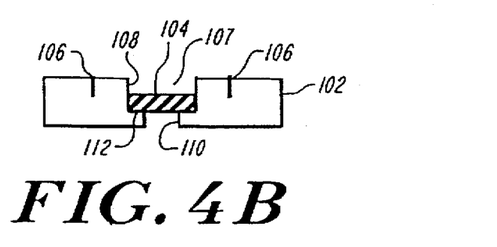
FIG. 4B shows a cross-sectional view of the sample holder of the present invention at 4B—4B of FIG. 4A.

A top view the sample holder of the present invention is shown in FIG. 4A. FIG. 4B is a cross-sectional view of the sample holder of the present invention at 4B—4B of FIG. 4A. Referring to these FIGS., body 102 of sample holder 100 serves as a structure upon which a sample may be placed. Body 102 has stepped opening 107 located in the center. Stepped opening 107 has upper section 108 and lower Section 110. Annular ledge 112 is formed between the two sections. Window 104 is disposed in the opening and is supported by annular ledge 112.

Samples to be analyzed are placed on Window 104. Analytical light illuminates the cells on the window to obtain spectral information. Window 104 of sample holder 100 is transparent to predetermined frequencies of light. Moreover, the window is porous so that water and materials dissolved in water will pass through it. The pores are not large enough, however, to permit passage of cells. In fact, the pores of the window will allow fluid to pass through the window at pressures that will not rupture window 104 or tear it from body 102 of the sample holder 100.

Body 102 also includes groove 106 disposed concentric with stepped opening 107. Groove 109 is for the attachment of a funnel (not shown) that is used for collecting cells from large volumes of fluid material, as will be described. Groove 116, however, is not required to practice the present invention.

Figure 5A:
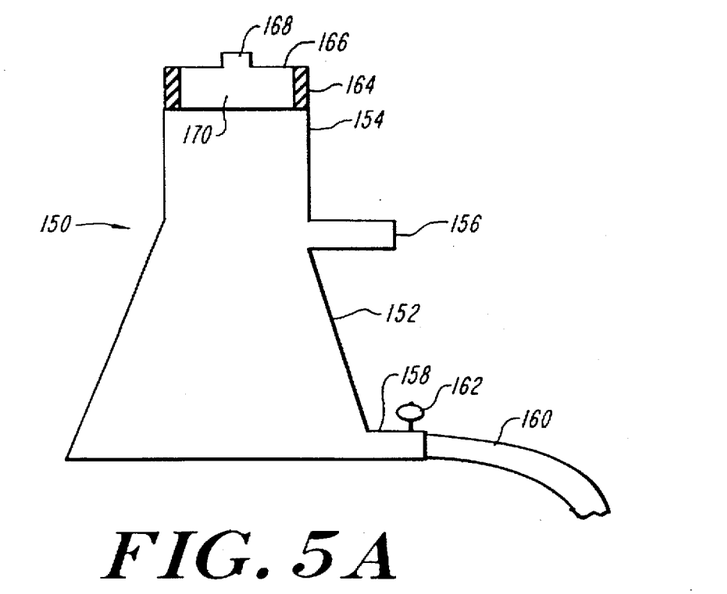
FIG. 5A shows the vacuum filtration system of the present invention.

Referring to FIG. 5A, the vacuum filtration system of the present invention is shown generally at 150. Vacuum filtration system 150 is used for loading cells in suspension onto window 104. Vacuum filtration system 150 includes vacuum flask 152 and frit 164 that is disposed in opening 154 at the top of vacuum flask 152.

Vacuum flask 152 has vacuum outlet 156 which is connected to a vacuum pump (no shown) that will draw a predetermined level of vacuum in vacuum flask 152. Vacuum flask 152 also has drain outlet 158 to which drain line 160 connects. Valve 162 is disposed in drain line 160 to control fluid drainage from vacuum flask 152.

Frit 164 has an outside contour and shape that permits it to sealingly fit in top opening 154 of vacuum flask 152. Frit 164 has top surface 166 and opening 170 in the bottom. Hollow nipple 168 extends upward from top surface 166. Hollow nipple is in fluid communications with opening 170. Frit 164, preferably is made from sintered glass.

Figure 5B:
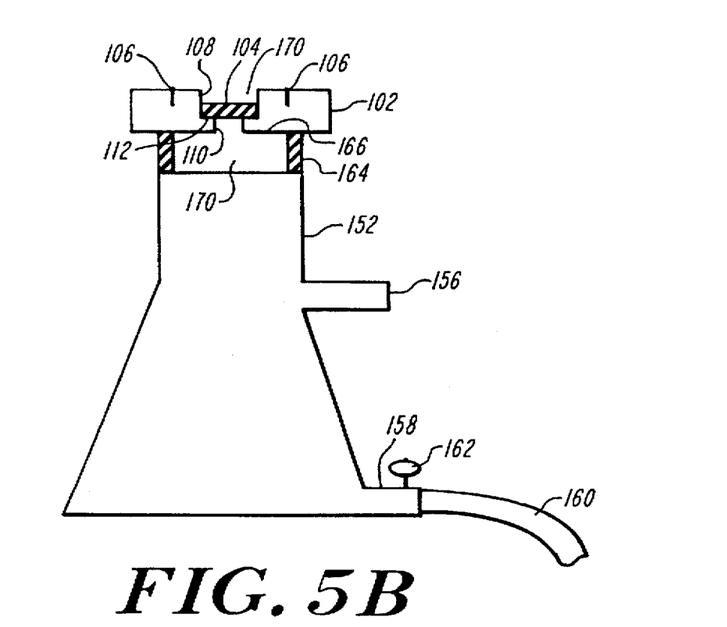
FIG. 5B shows the vacuum filtration system of FIG. 5A with the sample holder of the present invention mounted on it.

Referring now to FIG. 5B, vacuum filtration system 150 is shown with sample holder 100 disposed on it. As is shown, hollow nipple 168 is dimensionally shaped to fit into lower section 110 of stepped opening 107 in body 102 of sample holder 100, and up against the bottom of window 104.

Even though the FIGS. 5A and 5B show frit 164 with hollow nipple 168 extending from up surface 166, the present invention contemplates other configurations of frit 164, which includes without limited a flat frit with an opening to accommodate the size of window 104 and window 104 is disposed flush with the bottom of body 102.

Again referring to FIGS. 5A and 5B, constructing frit 164 to the exact contour of body 102 and window section 110 of the sample holder 100 insures efficient application of suction pressure through window 104. As such, negative pressure that is applied through vacuum flask 152 does not rupture the window or tear it from body 102. Therefore, all that happens when the vacuum is applied through causing suction through vacuum outlet 156 is window 104 of sample holder 100 is drawn tightly to the surface of the sintered glass frit 164.

Cells in suspension may be added to the center of the window by any convenient method such as by a pipette (not shown). The existence of upper section 108 of stepped opening 107 prevents the wetting of body 102 of sample holder 100 as suspensions of cells are added to window 104.

As the cells in a fluid medium are added to window 104, the fluid medium and dissolved components are drawn through the pores of window 104 by vacuum pressure. Since the pores of window 104 have the appropriate size, the cells become trapped at the surface of window 104. The fluid suspension is added to window 104 at a rate that will permit the fluid medium to filter through window 104 and collect in vacuum flask without wetting the sample holder. This novel configuration allows for the simultaneous concentration and addition of cells to window 104. Accordingly, there is no need to concentrate the cells in the suspension prior to adding them to window 104 of a sample holder 100.

Another aspect of the vacuum filtration system 150 is that the simultaneous addition of cells to window 104 and drying of such cells is accomplished by application of negative pressure to flask 152. As such, window 104 of sample holder 100 facilitates the processing of cells for spectral examination by rapidly and inexpensively collecting and concentrating the cells. Once cells have been added to window 104 of the sample holder 100, the cells are analyzed using infrared and/or Raman spectroscopy.

Referring to FIGS. 4A, 4B, 5A and 5B, aspects of sample holder 100 will be described in greater detail. Body 102 of sample holder 100 preferably is constructed of a molded plastic. However, it is understood that other methods may be used. For example, body 102 of sample holder 100 could be constructed of paper or cardboard, or other suitable material. Window 104 may be constructed of any suitable material that has the necessary optical properties for vibrational spectroscopy. This material also must be porous. The upper limit to the pore size must be less than the diameter of cells. Examples of suitable materials for window 104 are microporous non-woven or fibrous webs of glass, polyethylene, polypropylene, and alumina. Preferably, body 102 and window 104 are each constructed of a material that is substantially transparent to infrared energy and/or Raman scattered radiation.

Window 104 may be thin for some application and thicker for others. The thickness depends on the optical limitations imposed by the type of analysis that is to be conducted and the nature of the material being analyzed. For example, windows constructed of polyethylene have strong vibrational bands in the mid-infrared region. If such windows are relatively thick in the 2–3 mm ranges, they will not transmit enough light in the mid-infrared to be useful. However, if these materials are thin sheets in 10 to 20 µm range, they are excellent windows for infrared spectroscopy of cells and tissues. By contrast, thick layers of glass, as windows, do not create any problem for near infrared spectroscopy, or Raman or resonance Raman spectroscopy.

Before the cells are analyzed, they may be washed to remove any materials which will impact negatively on the spectral response from the cells or materials under analysis. Washing of the cells may be accomplished by using a pipette of wash solution of any volume. The washing step is repeated until the undesired materials are washed from the cells.

The fixation of cells provides a method to obtain a better response from the vibrational spectroscopic analysis of cells. Fixation is not used primarily in structures in which spectral examinations are conducted immediately after the collection of cells, otherwise fixation is a preferred method. However, in an automated system of analysis, in which cells from several samples are prepared and allowed to stand prior to examination by a spectrometer, e.g., in large central laboratories, fixation is used to assist in securing the successful use of spectroscopic methods to large numbers of samples.

Another method of processing the cells to be analyzed is to freeze them until they are prepared for examination by vibrational spectroscopy. Once unfrozen the cells are then prepared and maintained at low temperatures until the time of analysis. This, however, adds enormous complexity and expense to the infrared or Raman spectroscopic examination of cells and tissues.

In cases when a fixative material is added to the cells, it is important to remove the fixative prior to spectral examination so that artifacts based on the fixative are not present. The fixative may be removed by washing cells as extensively as desired once they are trapped on window 104 of sample holder 100. Specifically, the fixative is removed by washing window 104 with appropriate solutions.

In collecting of cervical cells, the cells are scraped from the cervix with brushes and spatulas. In preparing standard cytological smears, the cells attached to the brushes and/or spatulas are smeared onto glass slides. For the purpose of spectral analysis, however, the collecting devices are placed in capped bottles containing a buffered salt solution plus a fixative. Vigorous shaking of the sealed bottles displaces the cells from the brushes and spatulas and suspends the cells in the fluid in the collecting bottles. The suspension of cells can be aspirated from the bottles and added to window 104 of sample holder 100. The cells are fixed when they are removed from the bottles in which they are collected.

Cells collected by fine needle aspiration from the bottles are aspirated into a fluid-filled syringe. The cells collected in this manner can be added directly to window 104 of sample holder 100. This may be done within seconds of cell collection. This action is shown in FIG. 6 at 200.

Figures 6, 8:
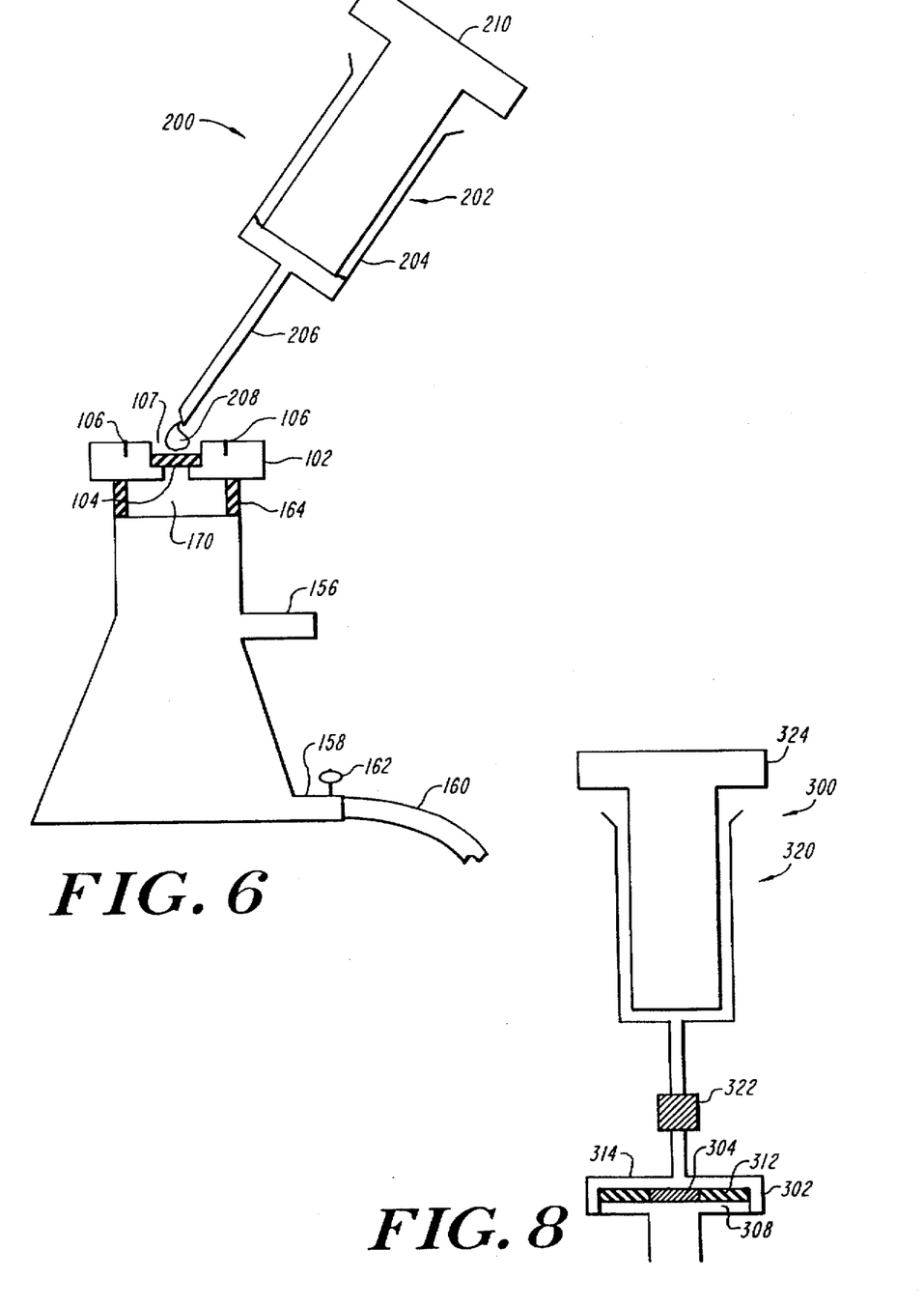
FIG. 6 shows a fluid suspension containing collected cells in a syringe with the fluid suspension being added to the sample holder of the present invention.
FIG. 8 shows a second embodiment of the system of the present invention for collecting and concentrating cells.

In FIG. 6, fluid 208 from syringe 202 is expelled from reservoir 204 through needle 206 upon positive pressure on plunger 210 of syringe 202. Cells can be fixed once they are placed on window 104 of sample holder 100 to avoid an intermediate step of adding the cells to fixative and then adding the suspension of cells in fixative to window 104. Preferably, fixation is accomplished by the addition of fixative to window 104 of sample holder 100. The vacuum is turned off to control the duration of contact between the fixative and the cells. After this period, the vacuum is turned on to remove the fixative. The excess fixative is then washed from the cells under vacuum by an appropriate wash solution. Also, once fixation is complete a series of washing steps take place to remove fixative from the cells.

The present invention facilitates the addition of cells to window 104 of sample holder 100 in a manner to speed up and simplify sample preparation for spectral analysis. The present invention also enhances the user's ability to remove biological substances from sample holder 100 that are of no interest spectrally or that might interfere with the spectral analysis of the cells. This could be, for example, the desire to diminish the amount of mucous in the sample on window 104. The user could do this by repeatedly washing the cells trapped on window 104 with large volumes of water or with a solution of normal saline. An alternative to simply washing away "contaminating material" of no spectral interest or material that might confound the spectra of the cells is to wash the window with chemical mixtures that react with contaminants. For example, again in the case of the desire to remove mucous, the cells trapped on the window can be washed with mucolytic agents to remove this mucous. In this regard, the contact time between wash liquid and cells trapped on window 104 can be controlled by varying the strength of the applied vacuum; this is especially valuable when the body is nonwettable as in the case of polyethylene, polypropylene, or other suitable hydrophobic materials.

According to the present invention, the preparation of the cells trapped on window 104 may be modified for desired purposes. Solutions containing vibrationally useful probes of surface molecules can be reacted with cells trapped on the window and then washed away prior to spectral analysis of the cells. This will provide means for enhancing or suppressing desired spectral aspects of the cells.

Also according to the present invention, it is possible to remove small cells from large cells on window 104. Samples of cervical cells often contain blood cells, which are quite small as compared with the size of cervical epithelial cells. Proper selection of the pore size in window 104 will allow for the separation of epithelial cells from blood cells. This will enhance the spectral analysis of the small numbers of epithelial cells in the presence of large numbers of contaminating blood cells.

The above examples apply to processing cells in relatively small volumes of body fluids, e.g. 1 to 2 ml or less. The present invention applies equally to processing cells in extremely dilute suspension in large volumes of body fluids. This is true even when there are liter amounts of fluids such as urine, ascites, pleural fluid, and cerebrospinal fluid, and the like in which a small number of cells reside. These larger fluid amounts can be easily added directly to window 104 of sample holder 100 without prior treatment of the cells or efforts to concentrate them in any way. The entire volume of fluid up to several liters, and all the cells suspended in a large volume, can be added to window 104 of sample holder 100, as will be described.

Figure 7:
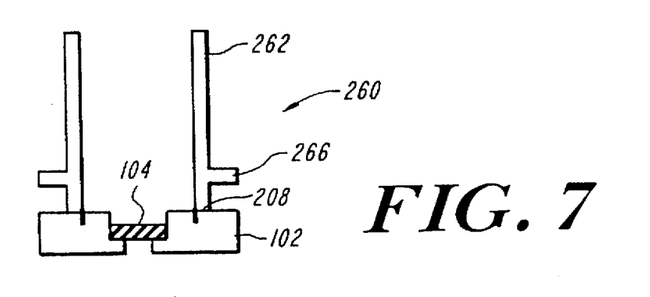
FIG. 7 shows the sample holder of the present invention with a detachable funnel connected to it.

Referring to FIG. 7, generally at 260, when large volumes of dilute suspensions of cells are to be processed, the sample holder and vacuum filtration system include detachable funnel 262 that is disposed in groove 106 in the top surface of body 102 of sample holder 100. Funnel 262 has bottom edge 208 that is dimensioned to fit into groove 106 in body 102. Spaced up from bottom edge 208 is circular flange 266 which is used for handling funnel 262. Funnel 262 prevents spillage and loss of cells.

FIG. 8 at 300 shows a second embodiment of the system for adding and concentrating cells on window 304 for vibrational spectroscopic analysis. In FIG. 8, window 304 is not attached permanently to body 308 of filter holder 302 but is free and is inserted into filter holder 302. Window 304 is disposed within filter holder 302 and filter holder 302 can be opened after use to remove window 304. Filter holder 302 may be made of any suitable material.

Preferably filter holder 302 includes frit 308 and cap 314. The frit and cap are made preferably from molded plastic. Cap 314 has a hollow member that extends upward from the top. Cap 314 and frit 308 sealably and detectability mate. Filter holder 302 holds window 304 in place and prevents it from tearing when positive pressure is applied.

Referring to FIG. 8, window 304 is bordered by nonporous frame 312 that is disposed on frit 308. Frame 312 restricts the cells collected on window 304 to small area and facilitates manipulation of window 304 after it is loaded with cells.

Figure 9:
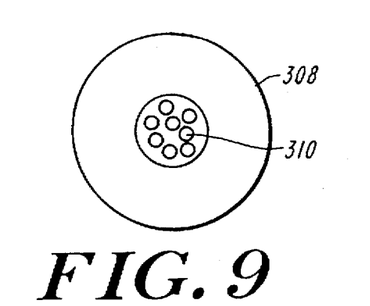
FIG. 9 shows a top view of the frit in the second embodiment of the system shown in FIG. 8.

FIG. 9 shows a top view of frit 308. Frit 308 is disposed below window 304 and has a plurality of openings 310 in fluid connections with the flask 152.

The member that extends upward from the top of cap 314 connects to syringe 320 via Luer lock 322 or any other suitable attachment mechanism. Plunger 324 is disposed in the top end of syringe 320 for forcing fluid with cells down to window 304. More specifically, the cells suspended in fluid medium within the barrel of the syringe 320 are collected on the window by applying positive pressure to plunger 324 of syringe 320 and filtering the suspension through window 304 that is held in filter holder 302. Once this is accomplished, window 304 with attached cells is removed from filter holder 302 by grasping window 304 via non-porous border 312. Filter holder 302 is discarded if it is made of plastic or other inexpensive materials or it can be washed for reuse if it is made of stainless steel or other expensive material.

Figure 11A:
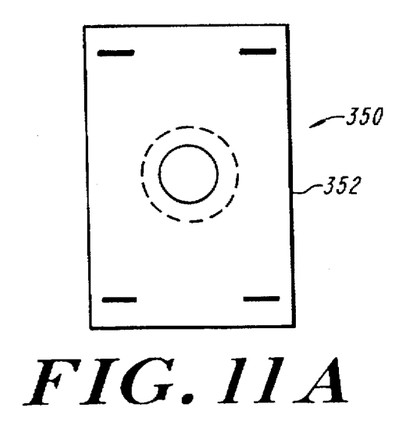
FIG. 11A shows a top view of a second embodiment of a sample holder of the present invention.
Figure 11B:
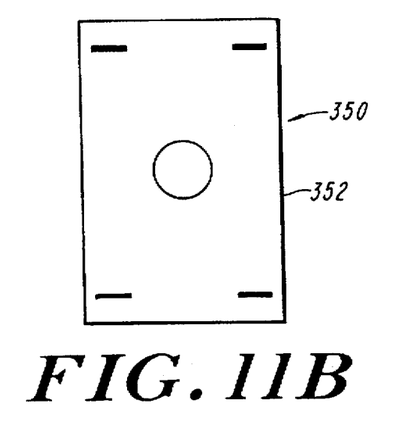
FIG. 11B shows a bottom view of the second embodiment of the sample holder of the present invention.

Window 304 with trapped cells is mounted on body 352 of disposable sample holder 350 that is shown in FIGS. 11A and 11B. FIG. 11A shows the top view and FIG. 11B shows the bottom view of the sample holder. Other methods for mounting window 304 on body 352 of sample holder 354 can be used. For example, window 304 may be mounted magnetically to a steel sample holder.

Figure 10:
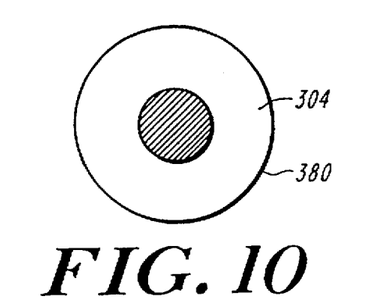
FIG. 10 shows a top view of the window and non-porous transport support.

Window 304 with trapped cells is removed from filter holder 302 and placed in infrared transparent support 380. This transparent support shown in FIG. 10, preferably is made from crystalline $CaF_2$ or other crystalline, infrared-transparent materials. Window 304 and support 380 may be mounted in standard infrared sample holder 354.

Figure 12:
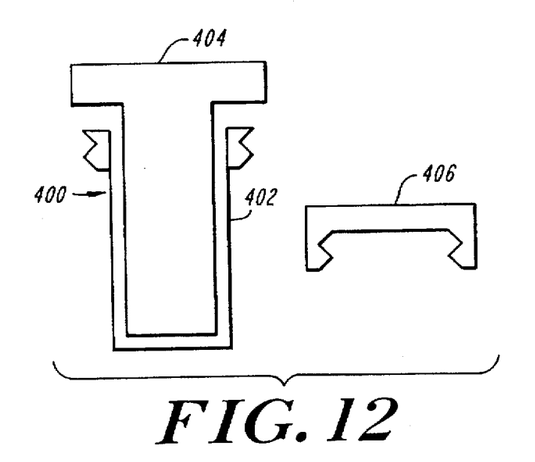
FIG. 12 shows an assembly for removing cells from collecting devices.

Referring to FIG. 12, an assembly is shown for removing cervical cells from brushes or spatulas. With plunger not removed from barrel 402 of modified syringe 400, the brush or spatula with cells attached is placed in the fluid medium in the barrel. Cap 406 is placed on the top of barrel 402 and the assembly is shaken to dislodge the cells from the collecting devices into the fluid medium. Cap 406 is removed and the collecting devices are removed from barrel 402. Next, the syringe is fitted with plunger 404. Plunger 406 is used to apply positive pressure on the fluid medium containing the cells.

Figure 13:
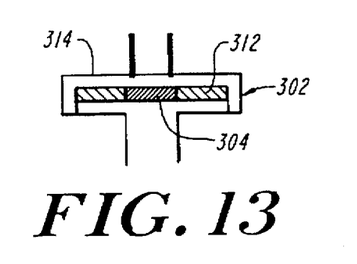
FIG. 13 shows a third embodiment of the system of the present invention for collecting and concentrating cells.

A third embodiment of the system for collecting and concentrating cells is shown in FIG. 13. This embodiment has an attached metal channel on cap 314 for puncturing the bottom of syringe 400 (FIG. 12). Positive pressure on plunger 404 of the syringe 400 will cause cells in the fluid medium to be applied to window 304. Alternatively, cervical cells in suspension, or any other type of cell in any type of collecting tube, are aspirated into a standard syringe. The standard syringe then is attached to filter holder 302 as in FIG. 8, and the cells in suspension are added to the window held within the filter holder.

Any of the manipulations of cells described with respect to embodiment of the invention depicted by FIGS. 4A, 4B, 5A and 5B can be applied to the embodiments in FIGS. 8–13. For example, cells can be fixed after they are trapped on the window within the filter holder by changing syringes and treating the window with appropriate fixative. The filter holder and syringe systems shown in FIGS. 8–13 can be used with fixed cells. When fixed cells are used, residual fixative is washed from the cells by changing the syringe to appropriate wash solution. Additionally, fixative or other reagents of potential use in the analysis of the cells can be present in the syringes to which cells are added.

Figure 14:
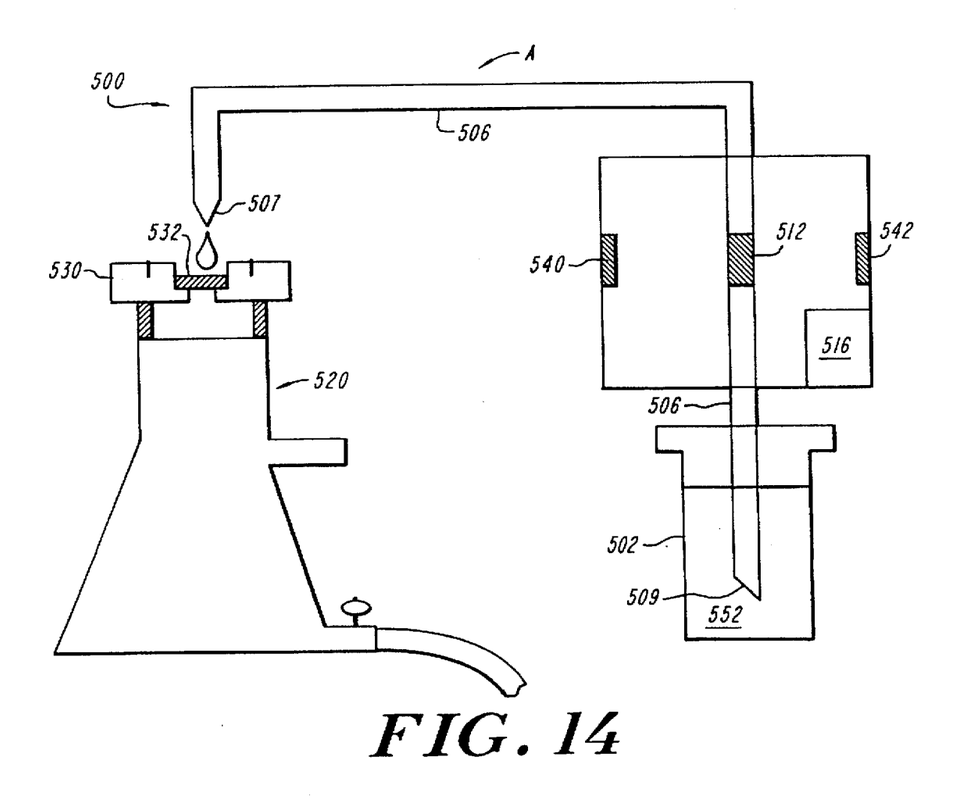
FIG. 14 shows a system and method for automatic or semi-automatic collection and concentrating cells.

Referring to FIG. 14 at 500, the system and method (automatic and semi-automatic) of the present invention will be described. After vigorous shaking to transfer cells from collecting devices to fluid suspension 552 in the collecting device 502, the system shown generally at 500 is used for manual or automatic collection and concentrating of cells for analysis. First end 509 of tube 506 is disposed in fluid suspension 552 in collecting device 502. Pump 516 causes the fluid medium to flow in direction "A" is tube 506. The cells are delivered to window 532 of sample holder 530 from end 507 of tube 506. The vacuum suction in flask 520 draws the fluid associated with the cells through the window and frit into the flask. This action may take place automatically. Preferably, the rate of aspiration for automatic operation substantially matches the rate of filtration, or the former is slower than the latter, to prevent spillage or waste of cells. All or the part cells may be added to window 532 in this way. The amount of cells to be added can be controlled by a device that controls the volume of the aspirate. Even this feature of the device can be controlled automatically, which is especially useful for controlling the amount of cells added to the window.

According to FIG. 14, there is continuous monitoring through a suitable optical window 512 of the aspirated stream in the flow path between aspirating pipette 506 and window 532 of sample holder 530. Window 512 may be observed visually or via the sensors at 540 and 542. The simplest method, in this regard, and the preferred embodiment of the present invention is to monitor turbidity by light scattering. Other ways to monitor the amount of cellular material in the stream are by absorption of protein or DNA, for example, but light scattering will be intense at short wavelengths. Independent of the optical method used to monitor the amount of cellular material in the stream of flow to window 532 of sample holder 530, a built-in program correlates flow rate for aspiration and the measurement of turbidity (or another optical property) to calculate the volume of suspension that must be added to window 532 to yield a sample with an optimal number of cells on window 532. When this volume of cells is added, aspiration is cut-off.

To facilitate a uniform distribution of cells in suspension, after shaking to displace them from the collecting devices, the collecting fluid is maintained at high density by addition of sucrose or other suitable material. Whatever material is used to increase the density of the collecting fluid and thereby to decrease the rate of settling of cells, it must be washed from the window after the requisite number of cells (based on measurements of turbidity) has been added to window 532. In the case that an inadequate number of cells has been added, after aspirating all the suspension, the system can provide a print out, a flashing light, or other suitable alarm (not shown) to show this condition.

In a large clinical pathology laboratory, complete automation of sample preparation can be obtained. In such operations, the bottles containing the cells are shaken automatically. Two sample holders, one for the endo- the other for the exocervical samples, are imprinted automatically with the same identifier code. Then the suspensions of endo- and exocervical cells are aspirated and added to the appropriate windows. Control of the number of cells added to each substrate is effected as described above and illustrated in FIG. 14. Once the cells are added, routines are carried out for washing cells and/or for treating the cells with fixatives, and for specific chemical treatments for specific modification of the cells, as described.

In FIG. 4, window 104 of sample holder 100 preferably has a diameter of approximately 3 mm. The beam of light in a standard infrared spectrometer is reduced to as small as 1.3 mm. With microscopic attachments, smaller light beams can be accomplished, down to the limit of diffraction effects. In the mid-infrared, the diffraction limit is greater than the dimensions of a single cell. In the near infrared, however, light beams the size of a cell can be produced, which applies as well to spectroscopy by Raman scattering.

Generally, spectra collected on cells represent an average spectrum of all cells in a sample. The capacity of vibrational spectroscopy to detect disease in cells and stage the severity of disease can be maximized by examining cells one at a time. To do so, requires that cells be added to a window such that the cells are spread out across the surface of the window. According to the present invention, the application of cells to the window provides a controlled method of adding cells to the window so that vibrational spectra can be collected simultaneously on a minimal number of cells at any one time or even one cell at a time. To do this, the aspirated cells in suspension are added to the window as shown in FIG. 14.

The drop-wise addition is controlled, as regards the size of the drops (which depend in part on the concentration of cells in the suspension) and their location on the window, by computer software that drives the tip of the pipette in small increments (as small as 1 µm, for example) across the horizontal and vertical dimensions of the window. Since the amount of fluid added at any one time is small and not allowed to spread across the window, the cells become "stuck" where they are deposited. The coordinates of the window at which cells are deposited are then used as a basis for washing the cells, again in drop-wise fashion or for treating cells as discussed above. Finally, the coordinates of location of cells on the window are fed on-line to the spectrometer, which has microscopic optics. The spectrometer collects and co-adds interferograms from each coordinate moving across and sampling multiple regions of the surface of the window. Software may direct the collection in this way on the basis of the stored coordinates for the positions of cells on the window. Each co-added spectrum is analyzed separately and simultaneously with the scanning of the window until the entire window has been scanned—cell by cell in some cases—or until a definitive diagnosis of disease can be made.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

I claim:
1. A system for preparation of cells, the sample holder being capable of removing such cells from suspension in fluids, the preparation including collecting and concentrating such cells, and further processing such cells so that useful vibrational spectra may be obtained from such cells:
 a central body that is transparent to at least infrared energy and Raman scattered radiation;
 a stepped opening through the central body;
 a porous window disposed in the stepped opening, with the window being at least transparent to infrared energy and Raman scattered radiation and including pores of a predetermined size extending through the window, with the window being capable of having cells prepared, which includes collecting, concentrating, and processing cells, at the window;
 an assembly for causing cells to be collected, concentrated, and processed on the window of the sample holder, with the assembly including,
 a container having an outlet for connection to a vacuum source, a second outlet for connection to a drain means, and a top end,
 a porous member that sealingly connects to the top end of the container and has a surface adapted to mate with the sample holder so that at least a part of the porous member is disposed beneath and adjacent to the window to operate in combination with the window for the preparation of cells, which includes collecting, concentrating, and processing cells, at the window.

2. The system as recited in claim 1, wherein the porous member has at least a portion that is dimensioned to fit against a predetermined portion of the window.

3. The system as recited in claim 2, wherein pores of the porous member have a size to permit fluid and material that pass through the window to pass through the porous member.

4. The system as recited in claim 3, wherein the porous member includes a frit.

* * * * *